(12) United States Patent
Gerlach et al.

(10) Patent No.: US 7,642,382 B2
(45) Date of Patent: Jan. 5, 2010

(54) PROCESSES FOR PREPARING ETHYLAMINES

(75) Inventors: Till Gerlach, Ludwigshafen (DE); Frank Haese, Dietzenbach (DE); Anton Meier, Birkenheide (DE); Johann-Peter Melder, Böhl-Iggelheim (DE); Heinz Rütter, Kapellen (BE)

(73) Assignee: BASF SE, Ludwigshafen (DE)

( * ) Notice: Subject to any disclaimer, the term of this patent is extended or adjusted under 35 U.S.C. 154(b) by 277 days.

(21) Appl. No.: 11/908,820

(22) PCT Filed: Mar. 14, 2006

(86) PCT No.: PCT/EP2006/060701

§ 371 (c)(1),
(2), (4) Date: Sep. 17, 2007

(87) PCT Pub. No.: WO2006/097468

PCT Pub. Date: Sep. 21, 2006

(65) Prior Publication Data

US 2009/0234163 A1 Sep. 17, 2009

(30) Foreign Application Priority Data

Mar. 15, 2005 (DE) ........................ 10 2005 012 209

(51) Int. Cl.
*C07C 209/16* (2006.01)
(52) U.S. Cl. ...................................... 564/480; 564/479
(58) Field of Classification Search ........................ None
See application file for complete search history.

(56) References Cited

U.S. PATENT DOCUMENTS 4,149,998 A    4/1979   Tauster et al.
4,760,190 A    7/1988   Twigg
7,563,933 B2 * 7/2009   Meier et al. ................. 564/480
2007/0167530 A1 7/2007  Gerlach et al.

FOREIGN PATENT DOCUMENTS

WO    WO-2005/063354 A1    7/2005
WO    WO-2005/063681 A1    7/2005
WO    WO-2006/092432 A2    9/2006

OTHER PUBLICATIONS

Eller, K., et al., "Amines, Aliphatic", Wiley-VCH Verlag GmbH & Co. KGaA, 2005, pp. 1-54.

* cited by examiner

*Primary Examiner*—Brian J Davis
(74) *Attorney, Agent, or Firm*—Connolly Bove Lodge & Hutz LLP

(57) ABSTRACT

Processes comprising: (a) providing a first reactant comprising a bioethanol; and (b) reacting the first reactant with a second reactant comprising a component selected from the group consisting of ammonia, primary amines, secondary amines and mixtures thereof, in the presence of hydrogen and a catalytically effective amount of a heterogeneous hydrogenation/dehydrogenation catalyst to form an ethylamine; wherein the catalyst has been activated at a temperature of 100 to 500° C. for at least 25 minutes; wherein prior to activation the catalyst comprises: (i) 20 to 65% by weight of a support material comprising one or both of zirconium dioxide ($ZrO_2$) and aluminum oxide ($Al_2O_3$), (ii) 1 to 30% by weight of oxygen-comprising compounds of copper, calculated as CuO, and (iii) 21 to 70% by weight of oxygen-comprising compounds of nickel, calculated as NiO; and wherein after activation the catalyst has a CO uptake capacity of >110 µmol of CO/g of the catalyst.

16 Claims, No Drawings

PROCESSES FOR PREPARING ETHYLAMINES

CROSS-REFERENCE TO RELATED APPLICATIONS

This application is a national stage application, under 35 U.S.C. §371, of PCT/EP2006/060701, filed Mar. 14, 2006, which claims priority of German Application No. 10 2005 012 209.4, filed Mar. 15, 2005.

BACKGROUND OF THE INVENTION

Processes for preparing an ethylamine by reacting ethanol with ammonia, a primary amine or a secondary amine are known to those skilled in the art from the literature, e.g. Ullmann's Encyclopedia of Industrial Chemistry, 6th Edition, 2000 electronic release, 'aliphatic Amines: Production from alcohols'.

The ethanol used can be prepared synthetically, for example by hydration of ethylene. An alternative to synthetic ethanol is biologically or biochemically produced ethanol, in particular ethanol produced by fermentation, known as bioethanol. This is prepared from renewable resources and is thus advantageous for ecological reasons. In addition, bioethanol is sometimes cheaper than synthetic ethanol.

However, when bioethanol was used over many amination catalysts, the catalyst deactivation was found to be significantly more rapid than was known in the use of synthetic ethanol.

As a result of the more rapid deactivation, the synthesis has to be interrupted more frequently in order to replace the catalyst. This leads to downtimes, increased costs for the catalyst and change in the catalyst and an increased personnel requirement combined with an increased accident risk.

If bioethanol is used in amination processes, the catalytically active metal surface of the respective heterogeneous catalyst becomes, as has been recognized according to the invention, coated to an increasing extent over time with the sulfur or sulfur compounds introduced via the bioalcohol. This leads to accelerated catalyst deactivation and thus to a significant deterioration in the economic viability of the respective process.

Synthetic ethanol generally has a content of sulfur and/or sulfur-comprising compounds of $\leq 0.1$ ppm by weight (calculated as S), e.g. determined by the Wickbold method (DIN EN 41).

The WO patent application having the application number PCT/EP/04/014591 of Dec. 22, 2004 (BASF AG) relates to a process for reducing the concentration of sulfur and/or a sulfur-comprising compound in a biochemically prepared organic compound, in which the respective organic compound is brought into contact with an adsorbent.

The WO patent application having the application number PCT/EP/04/014588 of Dec. 22, 2004 (BASF AG) relates to a process for preparing an ethylamine by reacting ethanol with ammonia, a primary amine or a secondary amine in the presence of hydrogen and a heterogeneous catalyst, in which a biochemically prepared ethanol (bioethanol) in which the concentration of sulfur and/or sulfur-comprising compounds has been reduced beforehand by bringing it into contact with an adsorbent is used.

BRIEF SUMMARY OF THE INVENTION

The present invention relates to a process for preparing an ethylamine by reacting ethanol with ammonia, a primary amine or a secondary amine in the presence of hydrogen and a heterogeneous catalyst.

The German patent application no. 102005010328.6 of Mar. 3, 2005 (BASF AG) relates to a process for reducing the concentration of sulfur and/or a sulfur-comprising compound from a sugar, a sugar alcohol and/or a sugar acid, in which the sugar, sugar alcohol and/or sugar acid in the liquid phase is brought into contact with an adsorbent.

It was an object of the present invention to discover an improved economical process for preparing an ethylamine from bioethanol, by means of which corresponding ethylamines, in particular monoethylamine, diethylamine and triethylamine, are obtained in high yield, space-time yield and selectivity.

In particular, the process should make increased catalyst operating lives possible in the synthesis of ethylamines.

(Space-time yields are reported in "amount of product/(catalyst volume·time)" $(kg/(l_{cat.} \cdot h))$ and/or "amount of product/(reactor volume·time)" $(kg/(l_{reactor} \cdot h))$.

Accordingly, we have found a process for preparing an ethylamine by reacting ethanol with ammonia, a primary amine and/or a secondary amine in the presence of hydrogen and a heterogeneous hydrogenation/dehydrogenation catalyst, wherein a biochemically or biologically prepared ethanol (=bioethanol) is used and the catalyst comprises one or more metals of group VIII and/or IB of the Periodic Table and after activation with hydrogen has a CO uptake capacity of >100 μmol of CO/g of catalyst.

The bioethanol used according to the invention is generally produced from agricultural products such as molasses, cane sugar juice, maize starch or from products of wood saccharification and from sulfate waste liquors by fermentation.

Preference is given to using bioethanol which has been obtained by fermentation of glucose with elimination of $CO_2$ (K. Weissermel and H.-J. Arpe, Industrial Organic Chemistry, Wiley-VCH, Weinheim, 2003, p. 194; Electronic Version of Sixth Edition of Ullmann's Encyclopedia of Industrial Chemistry, 2000, Chapter Ethanol, Paragraph Fermentation).

The ethanol is generally isolated from the fermentation broths by distillation methods: Electronic Version of Sixth Edition of Ullmann's Encyclopedia of Industrial Chemistry, 2000, Chapter Ethanol, Paragraph 'Recovery and Purification'.

In particular and advantageously, a biologically or biochemically prepared ethanol (bioethanol) in which the concentration of sulfur and/or sulfur-comprising compounds has not been reduced beforehand, e.g. by bringing it into contact with an adsorbent such as silica gel, an activated aluminum oxide, a zeolite having hydrophilic properties, an activated carbon or a carbon molecular sieve, is used in the process of the invention.

DETAILED DESCRIPTION OF THE INVENTION

The process of the present invention is preferably carried out using a bioethanol which has a content of sulfur and/or sulfur-comprising compounds of $\geq 0.5$ ppm by weight, or $\geq 1$ ppm by weight, or $\geq 2$ ppm by weight, or $\geq 5$ ppm by weight, or $\geq 10$ ppm by weight (in each case calculated as S), e.g. determined by the Wickbold method (DIN EN 41) (for S contents of $\leq 2$ ppm by weight) or determined coulometrically in accordance with DIN 51400 part 7 (for S contents of >2 ppm by weight).

The content of sulfur and/or sulfur-comprising compounds can be, for example, up to 10 ppm by weight, up to 50 ppm by weight, up to 100 ppm by weight or up to 200 ppm by weight (in each case calculated as S), e.g. determined coulometrically in accordance with DIN 51400 part 7.

Particular preference is given to using a bioethanol which has a content of sulfur and/or sulfur-comprising compounds in the range from ≧0.5 to 2 ppm by weight (calculated as S), e.g. determined by the Wickbold method (DIN EN 41).

The sulfur-comprising compounds are inorganic compounds such as sulfates, sulfites, and/or organic compounds, in particular symmetrical or unsymmetrical $C_{2-10}$-dialkyl sulfides, particularly $C_{2-6}$-dialkyl sulfides such as diethyl sulfide, di-n-propyl sulfide, diisopropyl sulfide, very particularly dimethyl sulfide, $C_{2-10}$-dialkyl sulfoxides such as dimethyl sulfoxide, diethyl sulfoxide, dipropyl sulfoxide, 3-methylthio-1-propanol and/or S-comprising amino acids such as methionine and S-methylmethionine.

In particular embodiments, use is made of a bioethanol which has, in addition to the abovementioned content of sulfur and/or sulfur-comprising compounds, a content of $C_{3-4}$-alkanols in the range 1-5000 ppm by weight, in particular 5-3000 ppm by weight, very particularly preferably 10-2000 ppm by weight, a content of methanol in the range 1-5000 ppm by weight, in particular 5-3000 ppm by weight, very particularly preferably 20-1000 ppm by weight, a content of ethyl acetate in the range 1-5000 ppm by weight, in particular 5-3000 ppm by weight, very particularly preferably 10-2000 ppm by weight, and a content of 3-methyl-1-butanol in the range 1-5000 ppm by weight, in particular 5-3000 ppm by weight, very particularly preferably 10-2000 ppm by weight.

The content of $C_{3-4}$-alkanols (e.g. n-propanol, isopropanol, n-butanol, isobutanol, tert-butanol), methanol, ethyl acetate and 3-methyl-1-butanol is determined, for example, by means of gas chromatography (30 m DB-WAX column, internal diameter: 0.32 mm, film thickness: 0.25 μm, FID detector, temperature program: 35° C. (5 min.), 10° C./min. heating rate, 200° C. (8 min.)).

The catalyst used in the process of the invention comprises one or more metals of group VIII and/or IB of the Periodic Table of the Elements.

Examples of such metals are Cu, Co, Ni and/or Fe, and also noble metals such as Ru, Pt, Pd, and also Re. The catalysts may be doped, for instance with Ag, Zn, In, Mn, alkali metals (Li, Na, Ka, Rb, Cs) and/or Mo.

As support material for these active metals, preference is given to using aluminum oxide (gamma, delta, theta, alpha, kappa, chi or mixtures thereof), silicon dioxide, zirconium dioxide, zeolites, aluminosilicates, etc., and mixtures of these supports.

The catalysts can be produced by known methods, e.g. by precipitation, precipitation onto a support, impregnation.

Particularly preferred heterogeneous catalysts for the amination of the bioethanol used comprise, in their catalytically active composition prior to treatment with hydrogen:

from 20 to 85% by weight, preferably from 20 to 65% by weight, particularly preferably from 22 to 40% by weight, of $Al_2O_3$, $TiO_2$, $ZrO_2$ and/or $SiO_2$, from 1 to 30% by weight, particularly preferably from 2 to 25% by weight, of oxygen-comprising compounds of copper, calculated as CuO, and from 14 to 70% by weight, preferably from 15 to 50% by weight, particularly preferably from 21 to 45% by weight, of oxygen-comprising compounds of nickel, calculated as NiO, with the molar ratio of nickel to copper preferably being greater than 1, in particular greater than 1.2, very particularly preferably from 1.8 to 8.5.

In a further variant, these particularly preferred catalysts further comprise, in their catalytically active composition prior to treatment with hydrogen:

from 15 to 50% by weight, particularly preferably from 21 to 45% by weight, of oxygen-comprising compounds of cobalt, calculated as CoO.

The oxygen-comprising compounds of copper, nickel and if appropriate cobalt, in each case calculated as CuO, NiO and CoO, of the preferred catalysts are generally comprised in the catalytically active composition (prior to treatment with hydrogen) in a total amount of from 15 to 80% by weight, preferably from 35 to 80% by weight, particularly preferably from 60 to 78% by weight, with the molar ratio of nickel to copper particularly preferably being greater than 1.

Further preferred heterogeneous catalysts for use in the process of the invention are:

catalysts which are disclosed in EP-A-382 049 (BASF AG) and whose catalytically active composition before the treatment with hydrogen comprises from 20 to 85% by weight, preferably from 70 to 80% by weight, of $ZrO_2$, from 1 to 30% by weight, preferably from 1 to 10% by weight, of CuO, and from 1 to 40% by weight, preferably from 5 to 20% by weight, each of CoO and NiO, for example the catalysts which are described in loc. cit. on page 6 and have the composition 76% by weight of Zr, calculated as $ZrO_2$, 4% by weight of Cu, calculated as CuO, 10% by weight of Co, calculated as CoO, and 10% by weight of Ni, calculated as NiO, and in particular catalysts which are disclosed in EP-A-963 975 (BASF AG) and whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar Ni:Cu ratio being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ and $MnO_2$, respectively, and no oxygen-comprising compounds of molybdenum, for example the catalyst A which is disclosed in loc. cit., page 17, and has the composition 33% by weight of Zr, calculated as $ZrO_2$, 28% by weight of Ni, calculated as NiO, 11% by weight of Cu, calculated as CuO and 28% by weight of Co, calculated as CoO, The catalysts produced can be stored as such. Before being used as catalysts in the process of the invention, they are prereduced by treating with hydrogen (=activation of the catalyst). However, they can also be used without prereduction, in which case they are then reduced (=activated) under the conditions of the process of the invention by the hydrogen present in the reactor.

To activate the catalyst, it is preferably exposed to a hydrogen-comprising atmosphere or a hydrogen atmosphere at a temperature in the range from 100 to 500° C., in particular from 150 to 400° C., very particularly preferably from 180 to 300° C., over a period of at least 25 minutes, in particular at least 60 minutes. The period for which the catalyst is activated can be up to 1 hour, preferably up to 12 hours, in particular up to 24 hours, very preferably up to 100 hours, and, for example, be in the range from 24 to 72 hours.

During this activation, at least part of the oxygen-comprising metal compounds present in the catalysts is reduced to the corresponding metals, so that these are present together with the various oxygen compounds in the active form of the catalyst.

The hydrogen-activated catalyst used in the process of the invention has a CO uptake capacity of >100 μmol of CO/g of catalyst. In particular, it has a CO uptake capacity of >110 μmol of CO/g of catalyst, very preferably >120 μmol of CO/g of catalyst, particularly preferably >130 μmol of CO/g of catalyst. The CO uptake capacity can be, for example, up to 1000 μmol of CO/g of catalyst, preferably up to 500 μmol of CO/g of catalyst.

To determine the CO uptake capacity of the catalyst, it is treated with carbon monoxide (CO) after it has been activated and the chemisorption of CO (=CO uptake capacity) is measured as follows.

Measurement of the CO Uptake Capacity:

A catalyst sample (about 0.3 g) is heated in a test tube at a rate of 5° C./min to 220° C. while passing hydrogen over the sample at a flow rate of 50 ml/min for 60 minutes. The sample is subsequently flushed with a stream of helium (flow rate: 50 ml/min) at 220° C. for 60 minutes. After this pretreatment, the chemisorption analysis is carried out at 30° C. using 20% by volume of CO in helium in accordance with the method of DIN 66136-3 (CO pulse chemisorption). The assumed stoichiometry factor for CO is 1. The amount of CO adsorbed is determined in accordance with DIN 66136-3.

The process of the invention is suitable, for example, for preparing ethylamines of the formula I

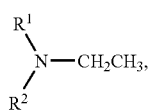

where
R$^1$, R$^2$ are each hydrogen (H), alkyl such as C$_{1-200}$-alkyl, cycloalkyl such as C$_{3-12}$-cycloalkyl, hydroxyalkyl such as C$_{1-20}$-hydroxyalkyl, aminoalkyl such as C$_{1-20}$-aminoalkyl, hydroxyalkylaminoalkyl such as C$_{2-20}$-hydroxyalkylamino-alkyl, alkoxyalkyl such as C$_{2-30}$-alkoxyalkyl, dialkylaminoalkyl such as C$_{3-30}$-dialkylaminoalkyl, alkylaminoalkyl such as C$_{2-30}$-alkylaminoalkyl, aryl, heteroaryl, aralkyl such as C$_{7-20}$-aralkyl or alkylaryl such as C$_{7-20}$-alkylaryl, or together form a —(CH$_2$)$_j$—X—(CH$_2$)$_k$— group,
X is CH$_2$, CHR$^3$, oxygen (O), sulfur (S) or NR$^3$,
R$^3$ is hydrogen (H), alkyl such as C$_{1-4}$-alkyl, alkylphenyl such as C$_{7-40}$-alkylphenyl, and
j, k are each an integer from 1 to 4.

The process of the invention is therefore preferably employed for preparing an ethylamine I by reacting the bioethanol with a nitrogen compound of the formula II

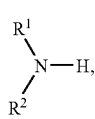

where R$^1$ and R$^2$ are as defined above.

Accordingly, the preparation of the ethylamine I involves purely formal replacement of a hydrogen atom of the nitrogen compound II by the radical CH$_3$CH$_2$— with liberation of one molar equivalent of water.

The substituents R$^1$ to R$^3$, the variable X and the indices j, k in the compounds I and II have, independently of one another, the following meanings:

R$^1$, R$^2$:
hydrogen (H),
alkyl such as C$_{1-200}$-alkyl, preferably C$_{1-20}$-alkyl, particularly preferably C$_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, in particular C$_{1-4}$-alkyl,
cycloalkyl such as C$_{3-12}$-cycloalkyl, preferably C$_{3-8}$-cycloalkyl such as cyclopropyl, cyclobutyl, cyclopentyl, cyclohexyl, cycloheptyl and cyclooctyl, particularly preferably cyclopentyl and cyclohexyl,
hydroxyalkyl such as C$_{1-20}$-hydroxyalkyl, preferably C$_{1-8}$-hydroxyalkyl, particularly preferably C$_{1-4}$-hydroxyalkyl such as hydroxymethyl, 1-hydroxyethyl, 2-hydroxy-ethyl, 1-hydroxy-n-propyl, 2-hydroxy-n-propyl, 3-hydroxy-n-propyl and 1-(hydroxymethyl)ethyl,
aminoalkyl such as C$_{1-20}$-aminoalkyl, preferably C$_{1-8}$-aminoalkyl such as amino-methyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl)aminomethyl,
hydroxyalkylaminoalkyl such as C$_{2-20}$-hydroxyalkylaminoalkyl, preferably C$_{3-8}$-hydroxyalkylaminoalkyl such as (2-hydroxyethylamino) methyl, 2-(2-hydroxy-ethylamino)ethyl and 3-(2-hydroxyethylamino)propyl,
alkoxyalkyl such as C$_{2-30}$-alkoxyalkyl, preferably C$_{2-20}$-alkoxyalkyl, particularly preferably C$_{2-8}$-alkoxyalkyl such as methoxymethyl, ethoxymethyl, n-propoxy-methyl, isopropoxymethyl, n-butoxymethyl, isobutoxymethyl, sec-butoxymethyl, tert-butoxymethyl, 1-methoxyethyl and 2-methoxyethyl, particularly preferably C$_{2-4}$-alkoxyalkyl,
dialkylaminoalkyl such as C$_{3-30}$-dialkylaminoalkyl, preferably C$_{3-20}$-dialkylamino-alkyl, particularly preferably C$_{3-10}$—N,N-dialkylaminoalkyl such as (N,N-dimethylamino)methyl, (N,N-dibutylamino)methyl, 2-(N,N-dimethylamino)ethyl, 2-(N,N-di-ethylamino)ethyl, 2-(N, N-dibutylamino)ethyl, 2-(N,N-di-n-propylamino) ethyl, 2-(N,N-diisopropylamino)ethyl, (R$^3$)$_2$N—(CH$_2$)$_q$ (q=1 to 6), very particularly preferably 3-(N,N-dimethylamino)propyl,
alkylaminoalkyl such as C$_{2-30}$-alkylaminoalkyl, preferably C$_{2-20}$-alkylaminoalkyl, particularly preferably C$_{2-8}$-alkylaminoalkyl such as methylaminomethyl, 2-(methylamino)ethyl, ethylaminomethyl, 2-(ethylamino) ethyl and 2-(isopropyl-amino)ethyl, (R$^3$)HN—(CH$_2$)$_q$ (q=1 to 6),
aryl such as phenyl, 1-naphthyl, 2-naphthyl, 1-anthryl, 2-anthryl and 9-anthryl, preferably phenyl, 1-naphthyl and 2-naphthyl, particularly preferably phenyl,
heteroaryl such as 2-pyridinyl, 3-pyridinyl, 4-pyridinyl, pyrazinyl, pyrrol-3-yl, imidazol-2-yl, 2-furanyl and 3-furanyl,
aralkyl such as C$_{7-20}$-aralkyl, preferably C$_{7-12}$-phenylalkyl such as benzyl, p-methoxybenzyl, 3,4-dimethoxybenzyl, 1-phenethyl, 2-phenethyl, 1-phenyl-propyl, 2-phenylpropyl, 3-phenylpropyl, 1-phenylbutyl, 2-phenylbutyl, 3-phenyl-butyl and 4-phenylbutyl, particularly preferably benzyl, 1-phenethyl and 2-phenethyl, alkylaryl such as $C_{7-20}$-alkylaryl, preferably $C_{7-12}$-alkylphenyl such as 2-methyl-phenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethyl-phenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, or two radicals together form a —$(CH_2)_j$—X—$(CH_2)_k$— group such as —$(CH_2)_3$—, —$(CH_2)_4$—, —$(CH_2)_5$—, —$(CH_2)_6$—, —$(CH_2)_7$—, —$(CH_2)$—O—$(CH_2)_2$—, —$(CH_2)$—$NR^3$—$(CH_2)_2$—, —$(CH_2)$—$CHR^3$—$(CH_2)_2$—, —$(CH_2)_2$—O—$(CH_2)_2$—, —$(CH_2)_2$—$NR^3$—$(CH_2)_2$—, —$(CH_2)_2$—$CHR^3$—$(CH_2)_2$—, —$CH_2$—O—$(CH_2)_3$—, —$CH_2$—$NR^3$—$(CH_2)_3$—, $R^3$:
hydrogen (H),
alkyl, in particular $C_{1-4}$-alkyl such as methyl, ethyl, n-propyl, isopropyl, n-butyl, isobutyl, sec-butyl and tert-butyl, preferably methyl and ethyl, particularly preferably methyl,
alkylphenyl, in particular $C_{7-40}$-alkylphenyl such as 2-methylphenyl, 3-methyl-phenyl, 4-methylphenyl, 2,4-dimethylphenyl, 2,5-dimethylphenyl, 2,6-dimethyl-phenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, X:
$CH_2$, $CHR^3$, oxygen (O), sulfur (S) or $NR^3$, preferably $CH_2$, NH and O, j:
an integer from 1 to 4 (1, 2, 3 or 4), preferably 1 and 2, and k:
an integer from 1 to 4 (1, 2, 3 or 4), preferably 1 and 2.

As aminating agent in the hydrogenative amination of the bioethanol in the presence of hydrogen, it is possible to use either ammonia or primary or secondary, aliphatic or cycloaliphatic or aromatic amines.

When ammonia is used as aminating agent, the alcoholic hydroxyl group is firstly converted into a primary amino group (—$NH_2$). The primary ethylamine formed in this way can react with further bioethanol to form the corresponding secondary amine (diethylamine) and this can in turn react with further alcohol to form the corresponding tertiary amine (triethylamine). Depending on the composition of the reaction batch or the feed stream (in the case of continuous operation) and depending on the reaction conditions employed, viz. pressure, temperature, catalyst, reaction time (space velocity over the catalyst), primary, secondary or tertiary ethylamines can be prepared preferentially in this way, depending on what is wanted.

Like ammonia, primary or secondary amines can be used as aminating agents.

These aminating agents are preferably used for preparing unsymmetrically substituted dialkylamines or trialkylamines such as ethyldiisopropylamine and ethyldicyclohexylamine.

For example, the following monoalkylamines and dialkylamines are used as aminating agents: methylamine, dimethylamine, ethylamine, diethylamine, n-propylamine, di-n-propylamine, isopropylamine, diisopropylamine, isopropylethylamine, n-butyl-amine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine.

Amines which are particularly preferably prepared using the process of the invention are, for example, monoethylamine (from ethanol and ammonia), diethylamine (from ethanol and monoethylamine), triethylamine (from ethanol and diethylamine), monoethylamine/diethylamine/triethylamine mixture (from ethanol and ammonia) and dimethylethylamine (from ethanol and dimethylamine).

The aminating agent can be used in stoichiometric, substoichiometric or superstoichiometric amounts relative to the alcoholic hydroxyl group to be aminated.

In the case of amination using primary or secondary amines, the amine is preferably used in an approximately stoichiometric amount or slightly superstoichiometric amount per mol of alcoholic hydroxyl group.

Ammonia itself is generally used in a 1.5- to 250-fold, preferably 2- to 100-fold, in particular 2- to 10-fold, molar excess per mol of alcoholic hydroxyl group to be reacted.

Larger excesses both of ammonia and of primary or secondary amines are possible.

The process of the invention can be carried out batchwise or preferably continuously as follows, with the catalyst preferably being present as a fixed bed in the reactor. However, the embodiment as a fluidized-bed reaction with upward and downward swirling motion of the catalyst material is likewise possible.

The amination can be carried out in the liquid phase or in the gas phase. Preference is given to a fixed-bed process in the gas phase.

When the amination is carried out in the liquid phase, the starting materials (alcohol plus ammonia or amine) are simultaneously passed in the liquid phase together with hydrogen over the catalyst, which is usually present in a preferably externally heated fixed-bed reactor, at pressures of generally from 5 to 30 MPa (50-300 bar), preferably from 5 to 25 MPa, particularly preferably from 15 to 25 MPa, and temperatures of generally from 80 to 300° C., preferably from 120 to 270° C., particularly preferably from 130 to 250° C., in particular from 170 to 230° C. Operation in either the downflow mode or the upflow mode is possible. The space velocity over the catalyst is generally in the range from 0.05 to 5 kg, preferably 0.1 to 2 kg, particularly preferably from 0.2 to 0.6 kg, of alcohol per liter of catalyst (bed volume) and hour. If appropriate, the starting materials can be diluted with a suitable solvent such as tetrahydrofuran, dioxane, N-methyl-pyrrolidone or ethylene glycol dimethyl ether. It is advantageous to heat the reactants before they are fed into the reaction vessel, preferably to the reaction temperature.

When the amination is carried out in the gas phase, the gaseous starting materials (alcohol plus ammonia or amine) are passed in a gas stream, preferably hydrogen, which is sufficiently large for vaporization over the catalyst in the presence of hydrogen at pressures of generally from 0.1 to 40 MPa (1 to 400 bar), preferably from 0.1 to 10 MPa, particularly preferably from 0.1 to 7 MPa. The temperatures for the amination are generally from 80 to 300° C., preferably from 120 to 270° C., particularly preferably from 160 to 250° C. It is possible for the gas stream to flow into the fixed bed of catalyst either from above or from below. The gas stream required is preferably obtained by means of recycle gas operation.

The space velocity over the catalyst is generally in the range from 0.01 to 2 kg, preferably from 0.05 to 0.5 kg, of alcohol per liter of catalyst (bed volume) and hour.

The hydrogen is generally fed to the reaction in an amount of from 5 to 400 l, preferably from 50 to 200 l, per mol of alcohol component, with the liter figures being in each case based on S.T.P.

Both when working in the liquid phase and when working in the gas phase, it is possible to employ higher temperatures and higher total pressures. The pressure in the reaction vessel, which is the sum of the partial pressures of the aminating agent, of the alcohol and of the reaction products formed and also, if applicable, of the solvent used at the temperatures indicated, is advantageously increased to the desired reaction pressure by injection of hydrogen.

Both when carrying out the process continuously in the liquid phase and when carrying it out continuously in the gas phase, the excess aminating agent can be circulated together with the hydrogen.

If the catalyst is present as a fixed bed, it can be advantageous in terms of the selectivity of the reaction to mix the shaped catalyst bodies in the reactor with inert packing elements, i.e. to "dilute" it. The proportion of packing elements in such catalyst preparations can be from 20 to 80, particularly from 30 to 60 and in particular from 40 to 50, parts by volume.

The water of reaction formed during the course of the reaction (in each case one mol per mol of alcohol group reacted) generally does not adversely affect the conversion, the reaction rate, the selectivity and the operating life of the catalyst and is therefore advantageously removed from the reaction product only in the work-up of the latter, e.g. by distillation.

After the product mixture from the reaction has advantageously been depressurized, the excess aminating agent and the hydrogen are removed and the amination products obtained (ethylamines) are purified by distillation or rectification, liquid extraction or crystallization. The excess aminating agent and the hydrogen are advantageously returned to the reaction zone. The same applies to any incompletely reacted bioalcohol.

The amines prepared using the process of the invention are suitable, inter alia, as intermediates in the production of fuel additives (US-A-3,275,554; DE-A-21 25 039 and DE-A-36 11 230), surfactants, drugs and crop protection agents, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerators and/or emulsifiers.

All ppm figures in this document are by weight.

EXAMPLES

Catalyst A

Composition: 4% by weight of CuO, 10% by weight of CoO, 10% by weight of NiO, balance: $Al_2O_3$.

CO uptake capacity: 36 μmol of CO/g of catalyst.

Catalyst B (According to the Invention)

Composition: 13% by weight of CuO, 28% by weight of CoO, 28% by weight of NiO, balance: $ZrO_2$.

CO uptake capacity: 135 μmol of CO/g of catalyst.

The CO uptake capacity was determined as described on page 6, lines 27 to 39.

2.0 kg or 2.8 kg of catalyst A or B, respectively, were in each case installed in a 5 liter reactor and activated in a stream of hydrogen as follows.

Catalyst B: heat to 280° C. over a period of 12 hours in a stream of 200 standard l/h of $H_2$ and reduce at 280° C. under atmospheric pressure for 24 hours. Then set to synthesis parameters.

Catalyst A: heat to 280° C. over a period of 24 hours in a stream of 100 standard l/h of $H_2$ and reduce at 280° C. under atmospheric pressure in a stream of 100 standard l/h of $H_2$ for 48 hours. Then set to synthesis parameters. (Standard l=standard liters=volume converted to S.T.P.).

An initial pressure of 66 bar was set by introduction of ammonia and bioethanol was then metered continuously into the gas stream so that a constant molar ratio of ammonia:bioethanol of 1.4:1 was maintained. The reactor temperature was set so that the condensed output comprised not more than about 3% by weight of residual bioethanol in addition to monoethylamine, diethylamine and triethylamine.

An initial temperature of 195° C. had to be set over catalyst A in order to achieve this. While 135 kg of bioethanol/kg of catalyst A were passed continuously over the catalyst during the further course of the reaction, the temperature had to be adjusted stepwise to 227° C. to keep the ethanol content of the output below 3% by weight.

Over catalyst B, setting of an initial temperature of 175° C. in the catalyst bed under otherwise identical conditions was sufficient to keep the ethanol content of the output below 3% by weight. Even after 135 kg of bioethanol/kg of catalyst B, the catalyst displayed no drop in activity at 175° C.

Examples of Commercial Bioethanol Grades

Various commercial bioethanol grades were analyzed for their sulfur content.

|  | Bio-EtOH 1 | Bio-EtOH 2 | Bio-EtOH 3 | Bio-EtOH 4 | Bio-EtOH 5 | Bio-EtOH 6 | Bio-EtOH 7 |
|---|---|---|---|---|---|---|---|
| Total S (ppm by wt.) | 0.6 | 1 | 0.6 | 8 | 2 | 49 | 2 |
| Sulfate S (ppm by wt.) | 0.33 | 0.43 | 0.2 | n.d. | 0.9 | 6 | 2 |

Total S = total sulfur (=content of sulfur and/or sulfur-comprising compounds, calculated as S); contents of >2 ppm were determined coulometrically in accordance with DIN 51400 part 7; total sulfur contents of ≦2 ppm were determined by the Wickbold method (DIN EN 41).
Sulfate S = sulfate sulfur, determined by ion chromatography using a method based on EN ISO 10304-2.
n.d. = not determined.

The invention claimed is:

1. A process comprising:
(a) providing a first reactant comprising a bioethanol; and
(b) reacting the first reactant with a second reactant comprising a component selected from the group consisting of ammonia, primary amines, secondary amines and mixtures thereof, in the presence of hydrogen and a catalytically effective amount of a heterogeneous hydrogenation/dehydrogenation catalyst to form an ethylamine;
wherein the catalyst has been activated at a temperature of 100 to 500° C. for at least 25 minutes; wherein prior to activation the catalyst comprises: (i) 20 to 65% by weight of a support material comprising one or both of zirconium dioxide ($ZrO_2$) and aluminum oxide ($Al_2O_3$), (ii) 1 to 30% by weight of oxygen-comprising compounds of copper, calculated as CuO, and (iii) 21 to 70% by weight of oxygen-comprising compounds of nickel, calculated as NiO; and wherein after activation the catalyst has a CO uptake capacity of >110 μmol of CO/g of the catalyst.

2. The process according to claim 1, wherein the bioethanol is produced by fermentation.

3. The process according to claim 1, wherein after activation the catalyst has a CO uptake capacity of >120 μmol of CO/g of catalyst.

4. The process according to claim 1, wherein after activation the catalyst has a CO uptake capacity of >130 μmol of CO/g of catalyst.

5. The process according to claim 1, wherein the catalyst comprises copper, cobalt and nickel.

6. The process according to claim 4, wherein the catalyst comprises copper, cobalt and nickel.

7. The process according to claim 1, wherein prior to activation the catalyst comprises: (i) 20 to 65% by weight of a support material comprising one or both of zirconium dioxide ($ZrO_2$) and aluminum oxide ($Al_2O_3$), (ii) 1 to 30% by weight of oxygen-comprising compounds of copper, calculated as CuO, (iii) 21 to 50% by weight of oxygen-comprising compounds of nickel, calculated as NiO, and (iv) 15 to 50% by weight of oxygen-comprising compounds of cobalt, calculated as CoO.

8. The process according to claim 7, wherein after activation the catalyst has a CO uptake capacity of >130 μmol of CO/g of catalyst.

9. The process according to claim 1, wherein the bioethanol has a content of sulfur and/or sulfur-comprising compounds of ≧0.5 ppm by weight, calculated as S.

10. The process according to claim 1, wherein the first and second reactants are reacted at a temperature of 80 to 300° C.

11. The process according to claim 1, wherein the first and second reactants are reacted in a liquid phase at a pressure of 5 to 30 MPa.

12. The process according to claim 10, wherein the first and second reactants are reacted in a liquid phase at a pressure of 5 to 30 MPa.

13. The process according to claim 1, wherein the first and second reactants are reacted in a gas phase at a pressure of 0.1 to 40 MPa.

14. The process according to claim 10, wherein the first and second reactants are reacted in a gas phase at a pressure of 0.1 to 40 MPa.

15. The process according to claim 1, wherein the activation of the catalyst is carried out with hydrogen at a temperature of 150 to 400° C. over a period of at least 60 minutes.

16. The process according to claim 1, wherein the ethylamine comprises one or more of monoethylamine, diethylamine and triethylamine.

* * * * *